United States Patent [19]

Blythin et al.

[11] Patent Number: 4,866,061

[45] Date of Patent: Sep. 12, 1989

[54] ARYL-SUBSTITUTED NAPHTHYRIDINE AND PYRIDOPYRAZINE DERIVATIVES

[75] Inventors: David J. Blythin, North Caldwell; Ho-Jane Shue, Pine Brook, both of N.J.

[73] Assignee: Schering Corporation, Kenilworth, N.J.

[21] Appl. No.: 193,330

[22] Filed: May 12, 1988

Related U.S. Application Data

[60] Division of Ser. No. 946,118, Dec. 23, 1986, Pat. No. 4,760,073, which is a continuation-in-part of Ser. No. 851,068, Apr. 11, 1986, abandoned.

[51] Int. Cl.$^4$ .................. A61K 31/38; A61K 31/395; C07D 471/04; C07D 253/06
[52] U.S. Cl. .................. 514/250; 514/242; 514/253; 514/254; 514/256; 514/269; 514/272; 514/273; 514/274; 514/275; 514/292; 514/293; 544/182; 544/238; 544/300; 544/310; 544/316; 544/317; 544/319; 544/320; 544/321; 544/324; 544/328; 544/331; 544/333; 544/405; 544/345; 546/81; 546/82; 546/83; 546/84
[58] Field of Search .............. 514/250, 300, 242, 253, 514/254, 256, 269, 272, 273, 274, 275; 544/182, 238, 300, 310, 316, 317, 319, 320, 321, 324, 328, 331, 333, 405, 345; 546/81, 84

[56] References Cited

U.S. PATENT DOCUMENTS

| | | | |
|---|---|---|---|
| 4,113,731 | 9/1978 | Winters et al. | 514/300 |
| 4,232,017 | 11/1980 | Winters et al. | 514/300 |
| 4,452,800 | 6/1984 | Sherlock | 514/300 |
| 4,492,702 | 1/1985 | Sherlock | 514/300 |
| 4,596,809 | 6/1986 | Sherlock | 514/300 |
| 4,628,055 | 12/1986 | Sherlock | 514/300 |

FOREIGN PATENT DOCUMENTS

| | | | |
|---|---|---|---|
| 0127135 | 12/1984 | European Pat. Off. | 514/300 |
| 2142013 | 1/1985 | United Kingdom | 514/300 |

OTHER PUBLICATIONS

Kaneko, Ch. et al., Chem. Pharm. Bull. 17(6) 1290–1294 (1969).
Fournier et al., Bulletin La Société Chimique De France, pp. 364–369, 1968.
Abstract 83-779956 for Japanese 58-144, 391.
Abstract 101:38382t (Chemical Abstracts vol. 101, 1984).

*Primary Examiner*—Mary C. Lee
*Assistant Examiner*—J. Richter
*Attorney, Agent, or Firm*—Henry C. Jeanette; Richard C. Billups; James R. Nelson

[57] ABSTRACT

Aryl-substituted naphthyridines and pyridopyrazines are disclosed which are useful in treating allergic reactions, inflammation, peptic ulcers and/or hyperproliferative skin disease. Pharmaceutical compositions and methods of treatment employing such compounds are also disclosed.

9 Claims, No Drawings

ARYL-SUBSTITUTED NAPHTHYRIDINE AND PYRIDOPYRAZINE DERIVATIVES

CROSS REFERENCE TO RELATED APPLICATIONS

This application is a divisional application of U.S. application Ser. No. 946,118, filed Dec. 23, 1986, now U.S. Pat. No. 4,760,073, which is in turn a continuation-in-part of U.S. application Ser. No. 851,068, filed Apr. 11, 1986, now abandoned, priority of which is claimed hereunder.

BACKGROUND OF THE INVENTION

This invention relates to tricyclic naphthyridine and pyridopyrazine derivatives and to methods for their preparation.

SUMMARY OF THE INVENTION

The compounds of this invention are free bases and pharmaceutically acceptable salts thereof having the structural formula I

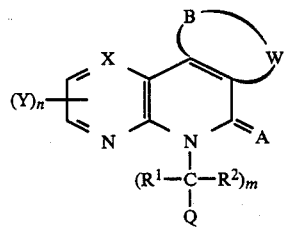

wherein:
X represents CH or N;
A represents O or S;
m is an integer of from 0 to 2;
n is an integer of from 0 to 2;
$R^1$ and $R^2$ are the same or different and each is independently selected from H or alkyl;
W represents a covalent bond or a group selected from —O—, —S(O)$_p$—, —NH—, —N($R^4$)—, —N(COR$^4$)—, or —N(SO$_2$R$^4$) {wherein p is an integer of from 0 to 2 and $R^4$ is alkyl};
B represents alkylene having from 2 to 8 carbon atoms, which alkylene may be optionally substituted with a group selected from —OH, —F, alkyl having from 1 to 4 carbon atoms, —CH$_2$OH, —CHO, —CO$_2$H, —COR$^3$ {wherein $R^3$ is selected from —NHR$^4$, —N(R$^4$)$_2$ or —OR$^4$ and $R^4$ is as defined above}, or —CN, with the proviso that OH or F is not on the carbon adjacent to W when W is —O—, —S(O)$_p$—, —NH—, —N(R$^4$)—, —N(COR$^4$)— or —N(SO$_2$R$^4$;
Q represents an aryl or an aromatic heterocyclic group which can optionally be substituted with up to 3 substituents Y as defined below; and
each Y substituent is independently selected from —OH, hydroxymethyl, alkyl, halo, —NO$_2$, alkoxy, —CF$_3$, —CN, cycloalkyl, alkynyloxy, alkenyloxy, —S(O)$_p$—R$^4$ {wherein R$^4$ and p are as defined above}, —CO—R$^5$ {wherein R$^5$ represents —OH, —NH$_2$, —NHR$^4$, N(R$^4$)$_2$ or —OR$^4$ in which R$^4$ is as defined above}, —O—D—COR$^5$ {wherein D represents alkylene having from 1 to 4 carbon atoms and R$^5$ is as defined above}, —NH$_2$, —NHR$^4$, —N(R$^4$)$_2$ {wherein R$^4$ is as defined above} or —NHCOH.

Compounds of formula I in which W is oxygen or a covalent bond are preferred. Also, A is preferably oxygen, while X is preferably CH. The group —B—W— preferably represents an alkylene or alkyleneoxy group, preferably —(CH$_2$)$_4$—, —(CH$_2$)$_5$—, —(CH$_2$)$_3$O— or —(CH$_2$)$_4$O—. Other suitable —B—W— groups include —CH(OH)(CH$_2$)$_3$—, —CH$_2$CH(OH)(CH$_2$)$_2$—, —(CH$_2$)CH(OH)CH$_2$—, —(CH$_2$)$_3$CHOH—, —CH(CH$_2$OH)(CH$_2$)$_3$—, —CH$_2$CH(CH$_2$OH)CH$_2$—, —(CH$_2$)$_3$CH(CH$_2$OH)—, —CH(OH)(CH$_2$)$_4$—, —CH$_2$CH(OH)(CH$_2$)$_3$—, —(CH$_2$)$_2$—CH(OH)(CH$_2$)$_2$—, —(CH$_2$)$_3$CH(OH)CH$_2$—, —(CH$_2$)$_4$CH(OH)—, —CH(CH$_2$OH)(CH$_2$)$_4$—, —CH$_2$CH(CH$_2$OH)(CH$_2$)$_3$—, —(CH$_2$)$_2$CH(CH$_2$OH)(CH$_2$)$_2$—, —(CH$_2$)$_3$CH(CH$_2$OH)CH$_2$—, —(CH$_2$)$_4$CH(CH$_2$OH)—, —CH(OH)(CH$_2$)$_2$O—, —CH$_2$CH(OH)CH$_2$O—, —CH(CH$_2$OH)(CH$_2$)$_2$O—, —CH$_2$CH(CH$_2$OH)CH$_2$O—, —(CH$_2$)$_2$CH(CH$_2$OH)O—, —CH(OH)(CH$_2$)$_3$O—, —CH$_2$CH(OH)(CH$_2$)$_2$O—, —(CH$_2$)$_2$CH(OH)CH$_2$O—, —CH(CH$_2$OH)(CH$_2$)$_3$O—, —CH$_2$CH(CH$_2$OH)(CH$_2$)$_2$O—, —(CH$_2$)$_2$CH(CH$_2$OH)CH$_2$O—, and —(CH$_2$)$_3$CH(CH$_2$OH)O—. The letter n preferably represents zero and m is preferably zero. Q is preferably phenyl or Y-substituted phenyl, and in the latter case each Y substituent on the Q phenyl ring is preferably selected from chloro, nitro, methoxy or trifluoromethyl. The most preferred orientation for nitro, methoxy and trifluoromethyl substituents is in the meta position.

A preferred subgenus is represented by the formula II

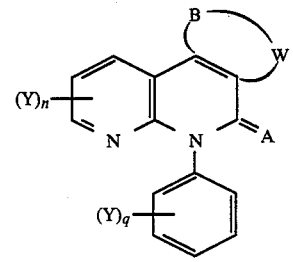

wherein A, H, W, n and Y are as defined above and q is 0 to 2.

When utilized herein, the terms below have the following scope:
halo—represents fluoro, chloro, bromo and iodo;
alkyl (including the alkyl portion of alkoxy) and alkylene—represent straight and branched carbon chains and, unless otherwise specified, contain from 1 to 6 carbon atoms;
alkenyloxy—represents straight and branched carbon chains having at least one carbon to carbon double bond and, unless otherwise specified, contains from 3 to 6 carbon atoms, the alkenyl group thereof being bonded to an adjacent structural element through an oxygen atom;
alkynyloxy—represents straight and branched carbon chains having at least one carbon to carbon triple bond and, unless otherwise specified, contains from 3 to 6 carbon atoms, the alkynyl group thereof being bonded to an adjacent structural element through an oxygen atom;

cycloalkyl—represents saturated carbocyclic rings having from 3 to 7 carbon atoms;

aryl—represents a carbocyclic group containing from 6 to 15 carbon atoms and having at least one benzene ring, with all available substitutable carbon atoms thereof being intended as possible points of attachment to the $(CR^1R^2)_m$ group or to the N atom if m is zero. More preferably, aryl is phenyl or Y-substituted phenyl. Suitable aryl groups include, e.g., phenyl, naphthyl, indenyl, indanyl, 3-chloroohenyl, 4-chlorophenyl, 4-fluorophenyl, etc.;

aromatic heterocyclic—represents cyclic groups having at least one O, S and/or N in the ring structure and having a sufficient number of delocalized pi electrons to provide aromatic character, with the aromatic heterocyclic groups containing from 3 to 14 carbon atoms, e.g., 2-, 3- or 4-pyridyl, 2- or 3-furyl, 2- or 3-thienyl, 2-, 4- or 5-thiazolyl, 2-, 4- or 5-imidazolyl, 2-, 4-, 5- or 6-pyrimidinyl, 2- or 3-pyrazinyl, 3- or 4-pyridazinyl, 3-, 5- or 6- [1,2,4-triazinyl], 2-, 3-, 4-, 5-, 6- or 7-benzofuranyl, 2-, 3-, 4-, 5-, 6- or 7-indolyl, 3-, 4- or 5-pyrazolyl, 2-, 4- or 5-oxazolyl, etc., with all available substitutable carbon atoms thereof being intended as a possible point of attachment to the $(CR^1R^2)_m$ group or to the N atom if m is zero.

The invention in its pharmaceutical composition aspect comprises a compound as described above in combination with a pharmaceutically acceptable carrier The invention also includes a method for treating allergic reactions in a mammal which comprises administering an anti-allergic effective amount of the above-defined pharmaceutical composition to the mammal The invention in a second pharmaceutical method aspect is a method for treating inflammation in a mammal which comprises administering an anti-inflammatory effective amount of the above-defined pharmaceutical composition to the mammal.

The invention in a third pharmaceutical method aspect is a method for treating peptic ulcers in a mammal which comprises administering a cytoprotective effective amount of the above defined pharmaceutical composition to the mammal.

The invention in a fourth pharmaceutical method aspect is a method for treating hyperproliferative skin diseases, e.g. psoriasis, lichenified eczema or seborrhoeic dermatitis, in a mammal which comprises topically administering an effective amount of the above-identified pharmaceutical composition to the mammal.

The invention in its process aspect is a method for converting a 3-spiro-4-keto-substituted naphthyridin-2-one or 7-spiro-8-keto-pyridopyrazin-6-one to a compound of formula I.

DETAILED DESCRIPTION OF THE INVENTION

The compounds of formula I contain a $-(CR^1R^2)_m-$ substituent wherein each $R^1$ group and each $R^2$ group may vary independently. Thus, for example, when m equals 2 the following patterns of substitution (wherein hydrogen and $CH_3$ are used to represent any substituent $R^1$ or $R^2$) are contemplated: $-C(CH_3)_2CH_2-$, $-CH_2C(CH_3)_2-$, $-CH_2CH(CH_3)-$, $-CH(CH_3)CH_2-$, $-(C(CH_3)H)_2-$ and the like.

As noted above, the compounds of the invention may include one or two Y substituents on the fused ring system. Also, the Q group may include up to three Y substituents depending upon the available sites for substitution. In compounds where there is more than one such Y substituent, they may be the same or different. Thus, compounds having combinations of different Y substituents are contemplated within the scope of the invention. Examples of suitable Y substituents include hydroxy, methyl, chloro, bromo, methoxy, cyclohexyl, allyloxy, 2-prooynyloxy, methylthio, methylsulfonyl, carboxy, acetoxy, N-methylaminocarbonyl, acetoxymethoxy, acetylamino, methylsulfonylamino and the like.

Compounds of the invention of formulas I and II can exist in unsolvated as well as solvated forms, including hydrated forms, e.g., hemihydrate. In general, the solvated forms, with pharmaceutically acceptable solvents such as water, ethanol and the like are equivalent to the unsolvated forms for purposes of this invention.

Certain compounds of the invention may exist in isomeric forms. The invention contemplates all such isomers both in pure form and in admixture, including racemic mixtures.

Certain compounds of the invention also form pharmaceutically acceptable salts with organic and inorganic acids, e.g., the pyrido- or pyrazino- nitrogen atoms may form salts with strong acid while compounds having basic Y substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their respective salt forms somewhat in certain physical properties, such as solubility in polar solvents, but the salts are otherwise equivalent to their respective free base forms for purposes of the invention.

Also, some compounds of this invention are acidic, e.g., when Y is OH, and can form salts with inorganic and organic bases.

The compounds of this invention may be synthesized from the corresponding 3-spiro-4-keto analogues of formula III below,

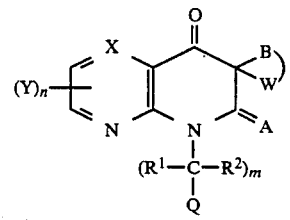

III which may be synthesized following the procedures described in copending U.S. application Ser. Nos. 561,416, filed Dec. 14, 1983 and 641,076, filed Aug. 15, 1984 and in EPO Publication No. 0 144 996, published June 19, 1985, the disclosures of which are hereby incorporated by reference for this purpose. Alternative synthetic routes for the synthesis of these starting materials and substitutional variants thereof may be accomplished by those skilled in the art.

This process involves a selective reduction of the 4-keto group of the compound of formula III followed by dehydration and rearrangement in the presence of a strong organic or inorganic acid. In particular, compound of formula III is selectively reduced at the 4 position using a reducing agent capable of reducing ketones in the presence of an amide function in an acidic medium, e.g., a hydride reducing agent, to produce a compound of formula IV

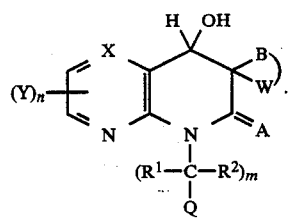
IV

Examples of suitable reducing agents for this step are sodium cyanoborohydride and tert-butylamine borane For a discussion of such selective reducing agents, see, for example, Herbert C. Brown, *Boranes in Organic Chemistry*, Cornell University Press, Ithaca and London, 1972, the relevant disclosure of which is hereby incorporated by reference. The reactions may be performed with cooling, with heating or at room temperature, as appropriate for the particular material being treated, e.g. at about 0° C. to about 40° C. Typically, the reaction is essentially complete in several minutes, but some reactions take several days to obtain maximum yield.

Suitable solvents are those which are capable of dissolving the starting materials and which do not react with the reducing agent to make the solution basic, of which aqueous alcohol and aqueous tetrahydrofuran in combination with a weak mineral or carboxylic acid, such as acetic acid, are examples.

The compounds according to structural formula IV are treated, either in their impure state or after suitable purification using techniques well known to those versed in the art, e.g., chromatography, with a strong organic or inorganic acid such as $H_2SO_4$, methanesulfonic acid, Eaton's reagent, polyphosphoric acid, etc., or strongly acidic salts such as $NaHSO_4$. I have found that super acids having a Hammett acidity function of less than about minus 12, i.e., minus 13, minus 14, etc., provide particularly advantageous results in this process. Suitable super acids include trifluoromethanesulfonic acid, $HF/BF_3$, $CH_3SO_3H/BF_3$, etc. This measure of acidity is defined in Hammett, Louis P., and Deyup, Alden J., *Journal of the American Chemical Society*, Vol. 54, 1932, p. 2721 The time and temperature of the reaction can vary depending on the acid employed. For example, with $CF_3SO_3H$ as the acid the temperature is generally in the range of from about room temperature (e.g., 25° C.) or below to about 150° C. Lower temperature (e.g., from about −78° C. to about 25° C.) may also be employed with for example, $HF/BF_3$. The acid is also generally used in excess, e.g., in an amount of from about 1.5 to about 30 equivalents. While not wishing to be bound to a specific mechanism, it appears that this treatment causes rearrangement of the spiro ring to form the ring

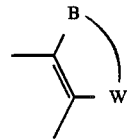

with the elimination of water, thus providing compounds of formula I. No diluent is required, but an inert cosolvent, such as a halohydrocarbon, e.g., methylene chloride, may be used.

Certain compounds of the invention can be prepared by an alternative reaction scheme employing as starting materials compounds of the formula V

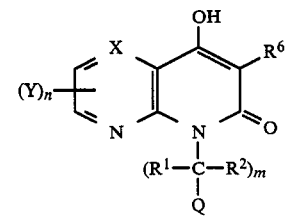
V wherein $R^1$, $R^2$, Q, X, Y, m and n are as defined above and $R^6$ is an alkyl group having from 2 to 8 carbon atoms Such compounds can be prepared as described in U.S. Pat. No. 4,492,702 or by reaction of a compound of the formula VI with a compound of formula VII

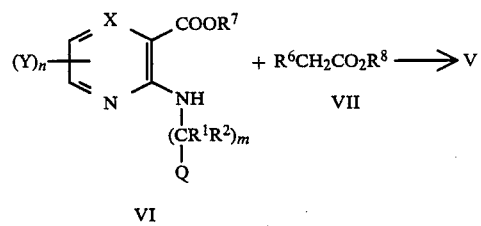

wherein $R^1$, $R^2$, $R^6$, Q, X, Y, m and n are as defined above and $R^7$ and $R^8$ are the same or different and are alkyl of from 1 to 8 carbon atoms.

In this alternative method, the compound of formula V is first reacted with an electrophilic halogenating agent, e.g., $Br_2$, $I_2+KI$, ICl, etc., to produce a compound of formula VIII:

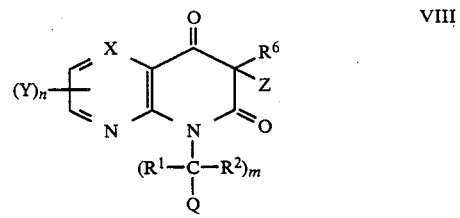
VIII wherein Z represents halo. This reaction can be performed in an inert solvent and at any suitable temperature, preferably, at room temperature or below.

The compound of formula VIII is subjected to a nucleophilic displacement with an alcohol, e.g., an alkanol such as methanol or an aralkanol such as benzyl alcohol. For example, the compound of formula VIII may be reacted with 1,8-diazobicyclo[5.4.0]undec-7-ene [DBU] and an alcohol, with the alcohol group replacing the halide group to produce a compound of formula IX

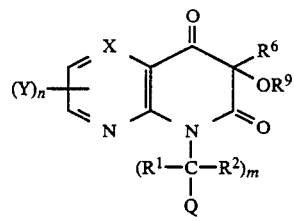

IX wherein $R^9$ is the residue of the alcohol, e.g. alkyl group such as methyl or aralkyl group such as benzyl This reaction may be conducted in an inert solvent and at any suitable temperature, again preferably at room temperature or below.

The compound of formula IX is reacted with a compound of the formula $M-(CR^{10}R^{11})_r CR^{12}=CR^{13}R^{14}$ {wherein M is an alkali metal such as Li or is Mg-Z where Z is a halo group; $R^{10}$, $R^{11}$, $R^{12}$, $R^{13}$ and $R^{14}$ may be the same or different and each is selected from H or alkyl having from 1 to 4 carbon atoms; and r is 0 or 1} to produce a compound of formula X

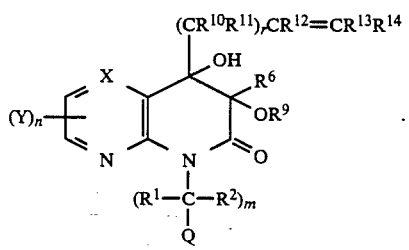

X

This reaction is performed under conventional conditions, e.g., in an inert solvent such as THF or diethyl ether and at any suitable temperature up to reflux.

The $R^9$ group is then removed with an ether cleaving reagent, e.g., $CF_3SO_3H$ $BBr_3$, $C_2H_5SH$ and $AlCl_3$, $K^+C_2H_5S^-$ in DMF, $Na^+C_2H_5S^-$ in DMF, etc., under conventional reaction conditions for such reactions to produce a compound of formula XI

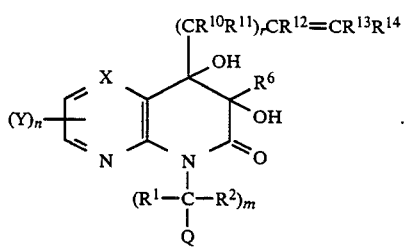

XI

The $R^6$ alkyl group is eliminated and a cyclization/-dehydration is effected by use of a strong organic or inorganic acid, such as $CF_3SO_3H$, polyphosphoric acid, Eaton's reagent, $P_2O_5$ in $CHCl_3$, etc., to produce an alkene from the $R^6$ group and a compound of formula XII

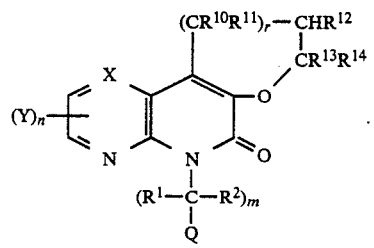

XII

When r is 1, the following isomer may also result:

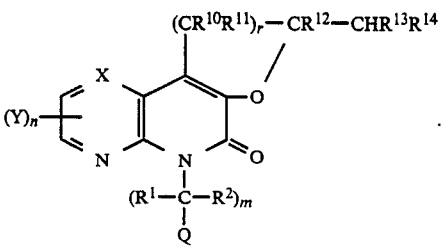

XIIa

This reaction can be performed neat or with an inert solvent and at any suitable temperature, preferably at room temperature or below.

In another method similar to that described in C. Keneko, T. Naito and M. Somei, *J.C.S. Chem. Comm.*, 804 (1979), a compound of formula XIII

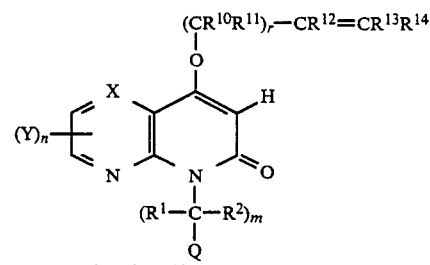

XIII

{wherein $R^1$, $R^2$, $R^{10}$, $R^{11}$, $R^{12}$, $R^{13}$, $R^{14}$, Q, X, Y, m, n and r are as defined above} can be irradiated with ultraviolet radiation, e.g., about 3000 Å, to produce a compound of formula XIV

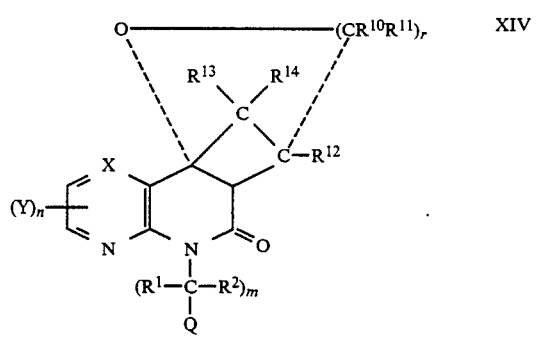

XIV

The compound of formula XIII is preferably in an inert solvent, e.g., an alcohol such as methanol or methanol/$CH_2Cl_2$, and the reaction mixture may be cooled during irradiation, if necessary. The starting compounds of formula XIII can be prepared by the methods described in U.S. Pat. No. 4,492,702.

The compound of formula XIV is reacted with a strong base such as a salt of an alcohol, e.g., a sodium or potassium alkoxide such as NaOCH₃, to produce a compound of formula XV

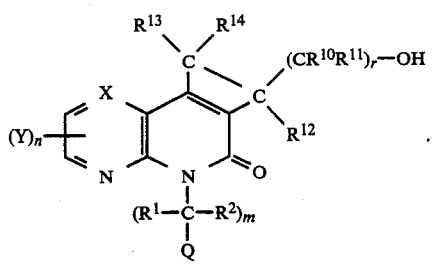

This latter reaction can be conducted in an inert solvent, e.g., an alcohol such as methanol, and at any suitable temperature, preferably at about 75° to about 125° C.

The compounds of this invention wherein A is sulfur may be obtained by treating the purified 2-carbonyl compound of formula I with thiating reagents well known in the art. Lawesson's Reagent {2,4-bis(4-methoxyphenyl-1,3-dithia-2,4-diphosphetane-2,4-disulfide} or one of its analogs, in toluene, or phosphorus pentasulfide in pyridine are suitable for this purpose.

For preparing pharmaceutical compositions from the compounds described by this invention, inert, pharmaceutically acceptable carriers are admixed with the active compounds. The pharmaceutically acceptable carriers may be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it may also be an encapsulating material In powders, the carrier is a finely divided solid which is in admixture with the finely divided active compound. In the tablet, the active compound is mixed with carrier having the necessary binding properties in suitable proportions and compacted in the shape and size desired. The powders and tablets preferably contain from 5 to about 70% of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter and other materials typically used in the pharmaceutical industries. The term "preparation" is intended to include the formulation of the active compound with encapsulating material as carrier, providing a capsule in which the active component (with or without other carriers) is surrounded by a carrier, which is thus in association with it. Similarly, cachets are included. Tablets, powders, cachets and capsules can be used as solid dosage forms suitable for oral administration.

For preparing suppositories, a low melting wax such as a mixture of fatty acid glycerides or cocoa butter is first melted and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection. Liquid preparations can also be formulated in solution or suspension in aqueous polyethylene glycol solution Aqueous solutions suitable for oral use can be prepared by adding the active component in water and adding suitable colorants, flavoring, stabilizing, sweetening, solubilizing and thickening agents as desired- Aqueous suspensions suitable for oral use can be made by dispersing the finely divided active component in water with viscous material, i.e., natural or synthetic gums, resins, methylcellulose, sodium carboxymethylcellulose and other well-known suspending agents.

Formulations for topical application may include creams, aerosols, sprays, dusts, powders, lotions and ointments which are prepared by combining an active ingredient according to this inventions with conventional pharmaceutical diluents and carriers commonly used in topical dry, liquid, cream and aerosol formulations. Ointments and creams may, for example, be formulated with an aqueous or oily base with the addition of suitable thickening and/or gelling agents. Such bases may, thus, for example, include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, etc.

Lotions may be formulations with an aqueous or oily base and will, in general, also include one or more of the following, namely, stabilizing agents, emulsifying agents, dispersing agents, suspending agents, thickening agents, coloring agents, perfumes and the like.

Powders may be formed with the aid of any suitable powder base, e.g. talc, lactose, starch, etc. DroDs may be formulated with an aqueous base or non-aqueous base also comprising one or more dispersing agents, suspending agents, solubilizing agents, etc.

The topical pharmaceutical compositions according to the invention may also include one or more preservatives or bacteriostatic agents, e.g., methyl hydroxybenzoate, propyl hydroxybenzoate, chlorocresol, benzalkonium chlorides, etc.

The topical pharmaceutical compositions according to the invention may also contain other active ingredients such as antimicrobial agents, particularly antibiotics, anesthetics, analgesics and antipruritic agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternatively, sufficient solid may be provided so that after conversion to liquid form, multiple individual liquid doses may be obtained by measuring predetermined volumes of the liquid form preparation as with a syringe, teaspoon or other volumetric container. The solid form preparations intended to be converted to liquid form may contain, in addition to the active material, flavorants, colorants, stabilizers, buffers, artificial and natural sweeteners, dispersants, thickeners, solubilizing agents and the like. The solvent utilized for preparing the liquid form preparation may be water, isotonic aqueous salt solutions, ethanol, glycerine, propylene glycol and the like, as well as mixtures thereof. The solvent utilized will be chosen with regard to the route of administration, for example, liquid preparations containing large amounts of ethanol are not generally suitable for parenteral use.

The compounds of the invention may also be deliverable transdermally for systemic distribution. The transdermal compositions can take the form of creams, lotions and/or emulsions and can be included in a transdermal patch of the matrix or reservoir type as are conventional in the art for this purpose.

Preferably, the pharmaceutical preparation is in unit dosage form. In such form, the preparation is subdivided into unit doses containing appropriate quantities of the active components. The unit dosage form can be a packaged preparation, the package containing discrete quantities of preparation such as packaged tablets, capsules and powders in vials or ampules. The unit dosage form can also be a capsule, cachet or tablet itself, or it may be the appropriate number of any of these in a packaged form.

The compounds of this invention may be employed as anti-allergy agents in the treatment of, for example, asthma, allergic or seasonal rhinitis, and/or chronic bronchitis. The anti-allergy method of this invention is identified by tests which measure a compound's inhibition of anaphylactic bronchospasm in sensitized guinea pigs having antigen induced broncho-constriction.

In one such test procedure, male Hartley guinea pigs (250–300 g) are sensitized with 5 mg ovalbumin injected i.p. and 5 mg injected s.c. in 1 ml saline on day 1 and 5 mg ovalbumin injected i.p. on day 4. The sensitized animals are used 3–4 weeks later at which time they weigh 450–500 g.

The sensitized guinea pigs are fasted overnight and the following morning are anesthetized with 0.9 ml/kg i.p. of dialurethane (0.1 g/ml diallybarbituric acid, 0.4 g/ml ethylurea and 0.4 g/ml urethane). The trachea are cannulated and the animals are ventilated by a Harvard® rodent respirator at 50 strokes/minute with a stroke volume of 5 ml. A side arm to the tracheal cannula is connected to a pressure transducer (Harvard) to obtain a continuous measure of intratracheal pressure which is recorded on a polygraph (Harvard). The jugular vein is cannulated for the i.v. administration of substances. The animals are challenged with antigen (0.5% ovalbumin) as an aerosol generated from a DeVilbiss® Model 65 ultrasonic nebulizer and delivered through the tracheal cannula for 30 seconds. Bronchoconstriction is measured as the peak increase in intratracheal pressure occurring within 5 minutes after antigen challenge.

The sensitized guinea pigs are injected i.v. with 1 mg/kg propranolol, 5 mg/kg indomethacin and 2 mg/kg mepyramine given together in a volume of 1 ml/kg. Fifteen minutes later the animals are challenged with nebulized ovalbumin. Test compounds are administered orally 2 hours before challenge with ovalbumin. Suppression of anaphylactic bronchospasm is expressed as a percent inhibition of the peak increase in intratracheal pressure by comparison to a vehicle-treated control group.

Four compounds of the invention tested in the above procedure were found to inhibit anaphylactic brochospasm as indicated in Table I below:

TABLE I

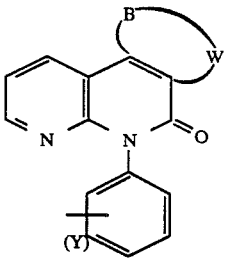

| Compound No. | Y | —B—W— | ED$_{50}$ (p.o.)-in anaphylactic bronchospasm test |
|---|---|---|---|
| 1 | m-Cl | —(CH$_2$)$_4$— | 2 mg/kg |
| 2 (hemihydrate) | H | —(CH$_2$)$_4$— | 2 mg/kg |
| 3 | m-Cl | —(CH$_2$)$_4$—O— | 5 mg/kg |
| 4 | H | —(CH$_2$)$_4$—O— | 1 mg/kg |

These compounds ere also found to inhibit allergen-induced histamine release from guinea pig and human sensitized tissue.

The compounds are effective non-adrenergic, non-anticholinergic, antianaphylactic agents. When administered orally they are active at doses from about 0.5 to 25 mg/kg of body weight, preferably 0.5 to 10 mg/kg; when administered parenterally, e.g., intravenously, the compounds are active at dosages of from about 0.1 to 5 mg/kg body weight preferably 0.1 to 2.5, and when administered by inhalation (aerosol or nebulizer) the compounds are active at dosages of about 0.1 to 5 mg per puff, one to four puffs may be taken every 4 hours.

The compounds of this invention are also useful for the treatment of inflammation. Thus, they are useful in the treatment of arthritis, bursitis, tendonitis, gout and other physical conditions characterized by inflammation. The anti-inflammatory use of the compounds of this invention may be demonstrated by the Reversed Passive Arthus Response Technique, as described below.

Reversed Passive Arthus Response (RPAR) Animals, Materials and Methods

Male Lewis inbred albino rats weighing 180–200 grams obtained from Charles River Breeding Laboratories are used in these experiments. The rats are housed 3 animals/cage and food and water are allowed ad libitum. The animals are numbered 1–3 in each cage and color marked for identification purposes.

Drug and Reagent Preparation

All reagents and drugs are prepared just prior to the study. Crystallized and lyophilized bovine serum albumin (BSA), available from Sigma Chemical Company, is solubilized without shaking in cold, sterile, pyrogen-free saline (10 mg/ml). Lyophilized anti-bovine serum albumin (IgG fraction), obtained from Cappel Laboratories, is suspended in sterile distilled water and diluted with cold, pyrogen-free saline (PFS) just prior to use. The final concentration of anti-bovine serum albumin is 0.5. mg/ml of PFS. Both BSA and anti-BSA solutions are iced during use. Drugs are suspended or solubilized in an aqueous solution of methyl cellulose (MC) with an homogenizer just prior to administration.

Drug Administration and Induction of Inflammation

Groups of animals (6/group) are dosed with drug in MC by gavage once daily for 3 days. The last dose is administered one hour prior to sensitization with BSA. Controls are given MC alone and a drug-standard is usually included in each assay for verification purposes. Drugs are prepared and diluted so as to provide a dose for a 200 gram animal which is equivalent to the mg/kg dose for each experiment. Thus each rat receives an oral dose in a volume of approximately 2.0 cc. One hour after the last dose the animals are lightly anesthetized with ether and "sensitized" by injection of 0.2 ml of PFS containing 1.0 mg of BSA into the penile vein. One hour later, the animals are "challenged" in the right rear paw with subplantar injections of 0.2 ml of ml of PFS containing 0.1 mg of anti-BSA. Immediately after the subplantar injection, the right paw is dipped (up to the lateral maleolus) into the mercury well of a plethysmograph. The volume of mercury displaced is converted to weight and recorded. This value is considered to be the control reading for the animal. Paw volumes are subsequently recorded with a plethysmograph during the development of the inflammation at 2 and 4 hours post-challenge.

Results

Results are expressed by the change in paw volume ($\Delta$ paw volume) from the control reading for each animal to that recorded 2 and 4 hours post-challenge. All drug treated groups are compared to the MC control for significant differences with an analysis of variance. Differences from control in drug-treated groups are expressed as percent chance from control in Table II.

TABLE II

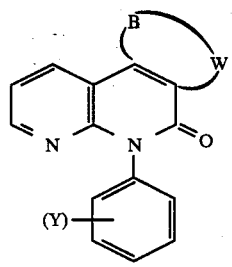

| Compound No. | Y | —B—W— | Dose(p.o) | Percent Inhibition vs. Control at 2 hrs. | at 4 hrs. |
|---|---|---|---|---|---|
| 1 | m-Cl | —(CH$_2$)$_4$— | 25 mg/kg | 64 | 30 |
| 2 (hemihydrate) | H | —(CH$_2$)$_4$— | 25 mg/kg | 75 | 29 |
| 4 | H | —(CH$_2$)$_4$O— | 25 mg/kg | 74 | 25 |

On the basis of the test results, an oral dosage range of from about 5 mg/kg of body weight per day to about 50 mg/kc of body weight per day in divided doses taken at about 4 hour intervals is recommended. The dosage to be administered and the route of administration depends upon the particular compound used, the age and general health of the patient and the severity of the inflammatory condition. Thus, the dose ultimately decided upon must be left to the judgment of a trained health-care practitioner.

The compounds of this invention are also useful in the treatment of peotic ulcers. They display chemotherapeutic activity which enables them to relieve the symptoms of peptic ulcer disease and stress ulceration, and to promote healing of gastric and/or duodenal ulcers. The antiulcer activity of the compounds of this invention is identified by standard tests which measure the cytoprotective effect in rats, e.g., by inducing gastrointestinal damage with ethanol prior to administering a compound of the invention. The compounds may be used as conjunctive therapeutic agents for coadministration with such anti-inflammatory/analgesic agents as aspirin, indomethacin, phenylbutazone, ibuprofen, naproxen, tolmetin and other agents. The compounds of this invention prevent the untoward side effects of irritation and damage to the gastrointestinal tract caused by such agents.

In the treatment of oeptic ulcer disease, and the prevention and treatment of drug-induced gastric ulceration, the active compounds of this invention can be administered in unit dosage forms such as tablets, capsules, pills, powders, granules, sterile parenteral solutions or suspensions, suppositories, mechanical delivery devices, e.g. transdermal, and the like. The compounds of this invention may be administered at doses of about 0.05–50 mg/kg of body weight per day. Preferably the total dosages are administered in 2–4 divided doses per day.

The compounds of formula I are useful in the treatment of hyperproliferative skin disease, e.g., psoriasis, which utility may be demonstrated by the Arachidonic Acid Mouse Ear Test as described below.

Arachidonic Acid Mouse Ear Test, Materials and Methods

Charles River, female, CD, (SD) BR mice, 6 weeks old, are caged 8/group and allowed to acclimate 1–3 weeks prior to use.

Arachidonic acid (AA) is dissolved in reagent grade acetone (2 mg/0.01 ml) and stored at $-20°$ C. for a maximum of 1 week prior to use. Inflammatory reactions are induced by applying 10 $\mu$l of AA to both surfaces of one ear (4 mg total).

Test drugs are dissolved in either reagent grade acetone or aqueous ethanol (only if insoluble in acetone) at the same doses selected by Opas et al., Fed. Proc. 43, Abstract 2983, p. 1927 (1984) and Young et al., J. Invest. Dermatol. 82, pp 367–371 (1984). These doses are employed to ensure maximum responses and to overcome any difference in topical absorption which could occur with any drug applied in an aqueous ethanol vehicle. The test drug is applied 30 minutes prior to challenge with AA.

The severity of the inflammation is measured as a function of increased ear weight. A 6 mm punch biopsy is removed 1 hour after AA challenge and weighed to the nearest 0.1 mg. Mean±standard error and all possible comparisons are made via Duncan's Multiple Range Statistic.

When administered for the treatment of hyperproliferative skin disease, the compounds of formula I may be administered topically, orally, rectally or parenterally. When administered topically, the amount of compound administered varies widely with the amount of skin being treated, as well as with the concentration of active ingredient applied to the affected area. When administered orally, the compounds of formual 1 are effective for the treatment of hyperproliferative skin disease at daily doses ranging from about 0.1 mg/kg to about 100 mg/kg, preferably from about 5 mg/kg to about 50 mg/kg, which may be administered in divided doses. When administered rectally, the compounds of formula I may be administered in daily doses ranging from about 0.1 mg/kg to about 100 mg/kg. When administered parenterally, the compounds of formula I are effective for the treatment of hyperproliferative skin disease in daily doses ranging from about 0.1 mg/kg body weight to about 10 mg/kg body weight which may be administered in divided doses.

As a result of the topical administration of a compound of formula I, a remission of the symptoms of the psoriatic patient, in most cases, can be expected. Thus, one affected by psoriasis can expect a decrease in scaling, erythema, size of the plaques, pruritus and other symptoms associated with psoriasis. The dosage of medicament and the length of time required for successfully treating each individual psoriatic patient may vary, but those skilled in the art of medicine will be able to recognize these variations and adjust the course of therapy accordingly.

Included within the invention are preparation for topical application to the skin whereby the compounds having structural formula I are effective in the treatment and control of skin diseases characterized by rapid rates of cell proliferation and/or abnormal cell proliferation, e.g. psoriasis.

In a preferred method of carrying out the invention, a pharmaceutical formulation comprising a compound of formula I together with a non-toxic, pharmaceutically acceptable topical carrier, usually in concentrations in the range of from about 0.001 percent to about 10 percent, preferably from about 0.1 percent to about 5 percent, is applied several times daily to the affected skin until the condition has improved. Topical applications may then be continued at less frequent intervals (e.g. once a day) to control mitosis in order to prevent return of severe disease conditions.

In all of the above modes of treatment, the dosage to be administered and the route of administration depends upon the particular compound selected, the age and general health of the subject, and the severity and type of condition to be controlled. Thus, the dose ultimately provided must be left to the judgment of a trained health-care practitioner.

The quantity of active compound in a unit dose preparation may be varied or adjusted from 1 mg to 100 mg according to the particular application and the potency of the active ingredient and the intended treatment. The composition may, if desired, also contain other therapeutic agents.

When administered parenterally, e.g. intravenously, the compounds are administered at a dosage range of about 0.1 to 5 mg/kg of body weight in single or multiple daily doses.

The invention disclosed herein is exemplified by the following preparative examples, which should not be construed to limit the scope of the disclosure. Alternative mechanistic pathways and analogous structures within the scope of applicants invention, may be apparent to those skilled in the art.

PREPARATIVE EXAMPLE 1

1'-(3-Chlorophenyl)-1',4'-dihydro-4'-hydroxy-spiro[cyclopentane-1,3'(2'H)-[1,8]-naphthyridin]-2'-one To a solution of 2.2 g (6.73 mmol.) of 1'-(3-chlorophenyl)-spiro[cyclopentane-1,3'-[1,8]-naphthyridin]-2',4'-(1'H)dione in 176 mL of (1:1) THF: EtOH (abs.) was added 2.54 g (40 mmol.) of NaBH$_3$CN and 3.0 mL of acetic acid. The solution was stirred at room temperature. An additional 0.2 g (3.2 mmol.) of NaBH$_3$CN and 0.3 mL of acetic acid were added on the fourth day. After 9 days the reaction was stopped by slow addition of 10 mL of water. After concentration, the residue was purified by column chromatography, eluting with CHCl$_3$—CH$_3$OH(95:5) to yield a colorless solid, 1.82 g. (5.53 mmol. 82%).

Recrystallization from CHCl$_3$ and diethyl ether (Et$_2$O) yielded the product, m.p. 144°–146° C.

PREPARATIVE EXAMPLE 2

(SR,RS)-1-(3-Chlorophenyl)-4-hydroxy-1,3',4,4',5',6'-hexahydro-spiro[1,8-naphthyridine-3(2H),2'[2H]-pyran]-2-one (Compound A) and
(RS,RS)-1-(3-Chlorophenyl)-4-hydroxy-1,3',4,4',5',6'-hexahydro-spiro[1,8,-naphthyridine-3(2H),2'[2H]-pyran]-2-one (Compound B)

To a solution of 1.0 g (2.92 mmol.) of 1-(4-chlorophenyl)-3', 4', 5', 6'-tetrahydro-spiro[1,8-naphthyridine-3,2'-[2H]-pyran]-2,4-dione in 80 mL of (1:1) THF/C$_2$H$_5$OH (abs.) was added 0.734 g (11.66 mmol.) of NaBH$_3$CN and 0.6 mL of acetic acid. The solution was stirred at room temperature for 5 days, then it was quenched by the addition of 5 mL of water. After concentration, the residue was purified by column chromatography over silica cel, eluting with CHCl$_3$—CH$_3$OH (95:5), to yield 1.06 g (95%) of a mixture of the diastereomers, Compounds A and B. These were separated by preparative reversed-phase HPLC, eluting with CH$_3$CNH$_2$O—CH$_3$COOH (30:70:1) to yield 0.52 g (54%) of Compound A, m.p. 183°–184.5° C., and 0.12 g (12%) of Compound B, m.p. 186.5°–188.5° C.

PREPARATIVE EXAMPLE 3

4-Hydroxy-1,3',4,4',5',6'-hexahydro-1-phenyl-spiro[1,8-naphthyridine-3(2H),2'[2H]-oyran]-2-one (mixture of diastereomers)

In a stirred mixture of tetrahydrofuran (THF) (200 mL) and C$_2$H$_5$OH (200 mL) was suspended 1-phenyl-3',4',5',6'-tetrahydro-spiro[1,8-naphthyridin-3,2'-[2H]-pyran]-2,4-dione (6.2 g) at room temperature. To the suspension was added acetic acid (2.6 mL) and tert-butylamine-borane (3.24 g).

After stirring for about 1 hour, water (ca. 200 mL) was added and the mixture was concentrated under vacuum to a volume of about 100 mL Additional water (400 mL) was added and the mixture was extracted with methylene chloride. The methylene chloride extract was separated, dried over sodium sulfate, filtered and concentrated. Ether was then added and the mixture was cooled. The resulting solid was removed by filtration, washed with fresh ether and dried to yield the desired product as a mixture of diastereomers, m.p. 211°–213° C.

By the methods described in Preparative Examples 1–3, the following compounds were prepared: 1',4'-Dihydro-4'-hydroxy-1'-phenyl-spiro[cyclopentane-1,3'-(2'H)[1,8]-naphthyridin]-2'-one, m.p. 148°–150° C.; and 1',4'-dihydro-4'-hydroxy-1'-phenyl-spiro[furan-2,3-(2'H)[1,8]-naphythridin]-2'-one, mixture of diastereomers, m.p. 220°–222° C.

EXAMPLE 1

7,8,9,10-Tetrahydro-5-phenyl-benzo[c][1,8]-naphthyridin-6-(5H)-one

A solution containing 1.2 g (4.07 mmol.) of 1',4'-dihydro-4'-hydroxy-1'-phenyl-spiro[cyclopentane-1,3'(2'H)-[1,8]-naphthyridin]-2'-one in 5.0 mL of trifluoromethanesulfonic acid was stirred at room temperature for 1.75 hours.

To this solution was added 100 mL of water and the resulting solution was adjusted to pH 5.0 with 2N NaOH. The precipitate was collected by filtration, washed with water, and redissolved in 200 mL of $CH_2Cl_2$. The organic solution was washed twice with 50 mL of saturated $NaHCO_3$ solution, then with 100 mL of $H_2O$, dried with $MgSO_4$, filtered, and concentrated in vacuo to yield 0.62 g (55%) of material, which was recrystallized from $CHCl_3/Et_2O$ to yield the desired product, m.p. 160°–162° C.

EXAMPLE 2

2,3-Dihydro-6-phenyl-1H-pyrano[2,3,-c][1,8]-naphthyridin-5(6H)-one, ¼ $H_2O$ To trifluoromethanesulfonic acid (5.0 mL) was added slowly, in portions, 1', 4'-dihydro-4'-hydroxy-1'-phenyl-spiro[furan-2,3-(2'H)-[1,8]-naphythyridin]-2'-one (1.0g) using a solid powder addition funnel, under $N_2$ at room temperature. The reaction was followed by HPLC and TLC which showed that one diastereomer rearranged faster than .the other but that both eventually disappeared, after a total of about 24 hours.

The resulting solution was poured into ice-water (200 mL) containing NaOH (2.26 g). The pH was then adjusted to 4 with 1 N HCl. The precipitate which formed on standing was collected, washed with water and purified by chromatography on silica gel (100 g), eluting with $CH_2Cl_2$ containing 2.5% of methanol, to yield the desired product, m.p. 250°–252° C.

In a similar manner, except for the length of time for which the reaction is run (progress followed by TLC), the following compounds were prepared:
5-(3-Chlorophenyl)-7,8,9,10-tetrahydro-benzo[c][1,8]-naphthyridin-6(5H)-one, m.p. 133°–135° C.;
7-Phenyl-1,2,3,4-tetrahydro-oxepino[2,3-c][1,8]-naphthyridin-6(7H)-one, m.p. 191°–193° C.; and
7-(3-Chlorophenyl)-1,2,3,4-tetrahydro-oxepino[2,3-c][1,8]-naphthyridin-6(7H)-one, m.p. 215°–217° C.

EXAMPLE 3

2,3-Dihydro-6-phenyl-1H-pyrano[2,3-c][1,8]-naphythyridin-5(6H)-thione.

A suspension of 2,3-dihydro-6-phenyl-1H-pyrano[2,3-c][1,8]-naphythyridin-5(6H)-one in dry toluene is stirred and heated in an $N_2$ atmosphere with a slight excess of Lawesson's Reagent [2,4-bis(4-methoxyphenyl)-1,3-dithia-2,4-diphosphetane-2,4-disulfide] at 50° C. then at gradually increasing temperatures (15° C. intervals, up to the reflux temperature) until TLC shows that reaction is occurring. Heating is continued until essentially no starting material remains; then the mixture is cooled, filtered, evaporated and purified by chromatography to yield the desired product.

By following the procedure of Example 3, or modifications well known to one skilled in the art, other sulfur-containing analogs of the invention may be produced.

EXAMPLE 4

1,2-Dihydro-5-phenylfuro[2,3-c][1,8]naphthyridin-4(5H)-one

Dissolve 3-n-butyl-4-hydroxy-1-phenyl-1,8-naphthyridin-2(1H)-one (10 g) in $CH_2Cl_2$ (1 L). Add a solution of $Br_2$ (1.74 mL, 5.43 g) in $CH_2Cl_2$ (30 mL) slowly. Stir briefly after the addition, then wash with water and evaporate. Recrystallize the intermediate bromo-compound (3-bromo-3-n-butyl-1-phenyl-1,8-naphthyridin-2,4(1H)-dione) from $CH_2Cl_2$/diethyl ether/hexane and redissolve it in $CH_2Cl_2$ (200 mL) and $CH_3OH$ (75 mL). Add DBU (12 mL, about 3 equiv.) and stir at room temperature. Evaporate off the solvents after about 1 hour and redissolve the residue in $CH_2Cl_2$ (750 mL). Add $H_2O$ and adjust the aqueous layer to pH of about 4 with 1N HCl. Dry with $MgSO_4$ and evaporate. Recrystallize the product (3-n-butyl-3-methoxy-1-phenyl-1,8-naphthyridin-2,4(1H)-dione) from diethyl ether/$CH_2Cl_2$ and purify, if necessary, by chromatography over silica gel, eluting with $CH_2Cl_2$ containing 5% ethyl acetate.

Dissolve the purified product (5 g) in dry tetrahydrofuran (THF) (50 mL) and cool to below 0° C. Add a slight excess of vinyl magnesium bromide (1 M in THF) and allow to react for 1 hour, then warm to room temperature. Add aqueous $NH_4Cl$ solution (50 mL), evaporate off the THF and extract into $CH_2Cl_2$ (2×50 mL). Wash with $H_2O$ (2x50 mL), dry with $Na_2SO_4$ and evaporate to yield a mixture of diastereomeric alcohols (diastereomers of 3-n-butyl-4-ethenyl-4-hydroxy-3-methoxy-1-phenyl-1,8-naphthyridin-2(1H)-one).

Dissolve the mixture in $CH_2Cl_2$ (50 mL) and cool to −78° C. Add a slight excess of $BBr_3$ in $CH_2Cl_2$ (10 mL) and stir for 1 hour. Allow to warm to room temperature, add $H_2O$ (25 mL) and adjust the pH of the aqueous layer to 4. Separate the organic layer, wash with water (2×25 mL), dry with $Na_2SO_4$, and evaporate. Dissolve the crude product (3-n-butyl-4-ethenyl-3,4-dihydroxy-1-phenyl-1,8-naphthyridin-2(1H)-one) in cold $CF_3SO_3H$ (below 0° C.) (20 mL) and stir until reaction is complete, as shown by HPLC analysis of a small sample. Allow to warm to room temperature, then pour into ice-water, adjust the pH to 4 and extract with $CH_2Cl_2$ (2×50 mL). Wash the organic layer with $H_2O$ (2×25 mL), dry with $MgSO_4$, evaporate and purify by column chromatography over silica gel, elutinc with increasing concentrations of ethyl acetate in $CH_2Cl_2$. Evaporate the fractions containing the product and recrystallize to yield the desired product.

EXAMPLE 5

1,2-Dihydro-2-(hydroxymethyl)-4-phenylcyclobuta(c)[1,8]naphthyridin-3(4H)-one A solution of 4-(2-propenyloxy)-1-phenyl-1,8-naphthyridin-2(1H)-one (1.0 g) in methanol (350 mL) under an atmosphere of nitrogen was irradiated at 3000 Å for 3½ days. Solvent was removed under vacuum and the reaction product purified by chromatography on silica gel in $CH_2Cl_2$ containing 10% ethyl acetate. The fractions containing the product were combined and evaporated to yield 3(S R),9b(R S)-3,3a-dihydro-5-ohenyl-3,9b-methano-2H-furo[3,2-c][1,8]naphthyridin-4(5H)-one, which was recrystallized from $CH_2Cl_2$/diethyl ether, m.p. 198°–199.5° C.

This compound (1.5 g) was dissolved in $CH_3OH$ (100 mL). To the solution was added sodium methoxide (320 mg) and the mixture was heated at 90° C. under a nitrogen atmosphere for about 2.5 hours. Solvent was removed under vacuum, the residue susoended in water, and the pH adjusted to 4 with 1 N HCl. The product was extracted with $CH_2Cl_2$ (3×100 mL) and the combined extracts washed with water (100 mL), dried with $MgSo_4$, and partially evaporated before separation on a silica gel chromatograohy column. The column was first eluted with $CH_2Cl_2$ containing 10% ethyl acetate, followed by $CH_2Cl_2$ containing 5% $CH_3OH$, and the product isolated from the relevant fractions, m.p. 204°–206° C.

By the methods of Examples 1–5 using suitably substituted reagents, the compounds according to Table III may be prepared.

PHARMACEUTICAL DOSAGE FORM EXAMPLES

EXAMPLE A

Tablets

| No. | Ingredient | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
|   | Total | 300 | 700 |

TABLE III

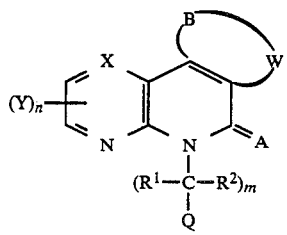

| X | n | Y* | m | $R^1$ | $R^2$ | A | B—W | Q |
|---|---|---|---|---|---|---|---|---|
| CH | 0 | — | 0 | — | — | O | $-CH_2CH_2CH_2O-$ | $C_6H_5-$ |
| CH | 0 | — | 0 | — | — | O | $-CH_2CH_2O-$ | $C_6H_5-$ |
| N | 0 | — | 0 | — | — | O | $-CH_2CH_2CH_2CH_2-$ | $C_6H_5-$ |
| N | 0 | — | 0 | — | — | O | $-CH_2CH_2CH_2CH_2-$ | $3-Cl-C_6H_4-$ |
| N | 0 | — | 0 | — | — | O | $-CH_2CH_2CH_2O-$ | $C_6H_5-$ |
| N | 0 | — | 0 | — | — | O | $-CH_2CH_2CH_2O-$ | $C_6H_5-$ |
| N | 0 | — | 0 | — | — | O | $-CH_2CH_2O-$ | $C_6H_5-$ |
| CH | 0 | — | 0 | — | — | S | $-CH_2CH_2CH_2O-$ | $C_6H_5-$ |
| CH | 0 | — | 0 | — | — | S | $-CH_2CH_2CH_2CH_2-$ | $C_6H_5-$ |
| CH | 1 | 7-$CH_3$ | 0 | — | — | O | $-CH_2CH_2CH_2O-$ | $4-CH_3O-C_6H_4-$ |
| CH | 0 | — | 0 | — | — | O | $-CH_2CH(OH)CH_2O-$ | $C_6H_5-$ |
| CH | 0 | — | 0 | — | — | O | $-CH_2CH(CH_2OH)CH_2-$ | $C_6H_5-$ |
| CH | 0 | — | 0 | — | — | O | $-CH_2CH_2CH(CH_2OH)O-$ | $C_6H_5-$ |
| CH | 0 | — | 0 | — | — | O | $-CH_2CH_2CH_2CH_2O-$ | $3-CH_3S-C_6H_4-$ |
| CH | 0 | — | 0 | — | — | O | $-CH_2CH_2CH_2CH_2-$ | $3-NO_2-C_6H_4-$ |
| CH | 0 | — | 0 | — | — | O | $-CH_2CH_2CH_2-$ | $3-Br-C_6H_4-$ |
| CH | 0 | — | 1 | H | H | O | $-CH_2CH_2CH_2N(CH_3)-$ | $3-CF_3-C_6H_4-$ |
| CH | 0 | — | 1 | $CH_3$ | H | O | $-CH_2CH_2CH_2-$ | 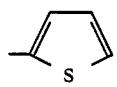 |
| CH | 1 | 6-Cl | 1 | H | H | O | $-CH_2CH_2CH_2-S^+(O-)-$ | $C_6H_5-$ |
| CH | 0 | — | 2 | H | H | O | $-CH_2CH_2CH_2O-$ | $4-F-C_6H_4-$ |
| CH | 0 | — | 1 | H | H | O | $-CH_2CH_2CH_2CH_2-$ | 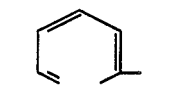 |
| CH | 0 | — | 1 | H | H | O | $-CH_2CH_2CH_2O-$ | 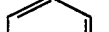 |

*Numbering based on 1,8-naphthyridine.

The following formulations exemplify some of the dosage forms of the compositions of this invention. In each, the term "active compound" designates 7-phenyl-1,2,3,4-tetrahydro-oxepino[2,3-c][1,8]-naphthyridin-6(7H)-one. It is contemplated, however, that this compound may be replaced by equally effective amounts of other compounds of formula I.

Method of Manufacture

Mix Item Nos. 1 and 2 in a suitable mixer for 10–15 minutes. Granulate the mixture with Item No. 3. Mill the damp granules through a coarse screen (e.g., ¼") if needed. Dry the damp granules. Screen the dried granules if needed and mix with Item No. 4 and mix for 10–15 minutes. Add Item No. 5 and mix for 1–3 minutes. Compress the mixture to appropriate size and weight on a suitable tablet machine.

EXAMPLE B

Capsules

| No. | Ingredient | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 4 | 7 |
|  | Total | 250 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

EXAMPLE C

Parenteral

| Ingredient | mg/vial | mg/vial |
|---|---|---|
| Active Compound Sterile Powder | 100 | 500 |

Add sterile water for injection or bacteriostatic water for injection, for reconstitution.

EXAMPLE D

Injectable

| Ingredient | mg/vial |
|---|---|
| Active Compound | 100 |
| Methyl p-hydroxybenzoate | 1.8 |
| Propyl p-hydroxybenzoate | 0.2 |
| Sodium Bisulfite | 3.2 |
| Disodium Edetate | 0.1 |
| Sodium Sulfate | 2.6 |
| Water for Injection q.s. ad | 1.0 ml |

Method of Manufacture (for 1000 vials)

1. Dissolve p-hydroxybenzoate compounds in a portion (85% of the final volume) of the water for injection at 65°–70° C.
2. Cool to 25°–35° C. Charge and dissolve the sodium bisulfite, disodium edetate and sodium sulfate.
3. Charge and dissolve active compound.
4. Bring the solution to final volume by added water for injection.
5. Filter the solution through 0.22 membrane and fill into appropriate containers.
6. Finally sterilize the units by autoclaving.

EXAMPLE E

Nasal Spray

|  | mg/ml |
|---|---|
| Active Compound | 10.0 |
| Phenyl Mercuric Acetate | 0.02 |
| Aminoacetic Acid USP | 3.7 |
| Sorbitol Solution, USP | 57.0 |
| Benzalkonium Chloride Solution | 0.2 |

|  | mg/ml |
|---|---|
| Sodium Hydroxide 1N Solution to adjust pH | — |
| Water Purified USP to make | 1.0 ml |

The following formulations exemplify some of the dosage forms in which the anti-psoriatic agents of the invention may be employed.

EXAMPLE F

Ointment

| Formula | mg/g |
|---|---|
| Active Compound | 1.0–20.0 |
| Benzyl Alcohol, NF | 20.0 |
| Mineral Oil, USP | 50.0 |
| White Petrolatum, USP to make | 1.0 g |

Method of Manufacture

Disperse active compound in a portion of the mineral oil. Mix and heat to 65° C., a weighed quantity of white petrolatum, the remaining mineral oil and benzyl alcohol, and cool to 50°–55° C. with stirring. Add the dispersed active compound to the above mixture with stirring. Cool to room temperature.

EXAMPLE G

Cream

| Formula | mg/g |
|---|---|
| Active Compound | 1.0–20.0 |
| Stearic Acid, USP | 60.0 |
| Glyceryl Monostearate | 100.0 |
| Propylene Glycol, USP | 50.0 |
| Polyethylene Sorbitan Monopalmitate | 50.0 |
| Sorbitol Solution, USP | 30.0 |
| Benzyl Alcohol, NF | 10.0 |
| Purified Water, USP to make | 1.0 g |

Method of Manufacture

Heat the stearic acid, glyceryl monostearate and polyethylene sorbitan monopalmitate to 70° C. In a separate vessel, dissolve sorbital solution, benzyl alcohol, water, and half quantity of propylene glycol and heat to 70° C. Add the aqueous phase to oil phase with high speed stirring. Dissolve the active compound in remaining quantity of propylene glycol and add to the above emulsion when the temperature of emulsion is 37°–40° C. Mix uniformly with stirring and cool to room temperature.

EXAMPLE H

Gel

| Formula | mg./g |
|---|---|
| Active Compound | 1.0–20.0 |
| Propylene Glycol, USP | 300.0 |
| Butylated Hydroxytoluene | 5.0 |
| Carbomer 940 | 5.0 |
| Sodium Hydroxide (added as a 1% w/w solution in propylene glycol) | 0.7 |
| Polyethylene Glycol 400, USP | 669.3–688. |

Method of Manufacture

Prepare a 1% solution of the sodium hydroxide in propylene glycol. Add approximately one-half the remaining propylene glycol and the polyethylene glycol to a suitable vessel and mix. Dissolve the butylated hydroxytoluene in this mixture. Disperse the carbomer 940 in the above mixture with vigorous agitation. Add the solution of sodium hydroxide with high speed agitation to bring pH up to 7 and mix until a thick gel forms. Dissolve the active compound in the remaining propylene glycol and add to the gel slowly as the gel is continuously mixed.

EXAMPLE I

Lotion

| Formula | mg/g |
| --- | --- |
| Active Compound | 1.0–20.0 |
| Carbomer 940 | 3.0 |
| Sodium hydroxide (charged as 4% w/w aqueous solution) | 0.05 |
| Isopropyl Alcohol | 40.00 |
| Purified Water, USP to make | 1.0 g |

Method of Manufacture

Prepare a 4% solution of sodium hydroxide in water. Heat the purified water to 60° C. Add carbomer 940 and mix at high speed until dispersed. Cool the above mixture to room temperature and slowly charge sodium hydroxide solution until uniform. Add 80% of isopropyl alcohol to the above with mixing. Dissolve the active compound in remaining isopropyl alcohol. Add this to the mixture with stirring. Adjust pH to 5.0 to 5.5 with sodium hydroxide, if necessary.

EXAMPLE J

Topical Aerosol

| Formula | mg/g |
| --- | --- |
| Active Compound | 1.0–20.0 |
| Caprylic/Capric Triglyceride | 50.00 |
| Mineral Oil | 20.00 |
| Denatured Alcohol | 150.00 |
| Hydrocarbon Aerosol Propellant q.s. ad. | 1.0 g |

Method of Manufacture

Add and mix the caprylic/capric triglyceride mineral oil and specially denatured alcohol in a suitable compounding tank. Add the active compound and continue mixing until the active compound is dissolved or dispersed uniformly. Fill the concentrate into cans and then fill the required amount of hydrocarbon aerosol propellant.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A compound having the structural formula

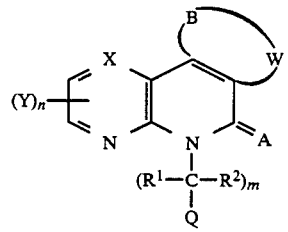

and pharmaceutically acceptable salts thereof, wherein:

X represents CH or N;

A represents O or S;

m is an integer of from 0 to 2;

n is an integer of from 0 to 2;

$R^1$ and $R^2$ are the same or different and each is independently selected from H or alkyl containing 1 to 6 carbon atoms;

W represents a covalent bond;

B represents alkylene having from 2 to 8 carbon atoms, which alkylene may be optionally substituted with a group selected from -OH, -F, alkyl having from 1 to 4 carbon atoms, —CH$_2$OH, —CHO, —CO$_2$H, —COR$^3$, {wherein R$^3$ is selected from —NHR$^4$, —N(R$^4$)$_2$, or —OR$^4$ and R$^4$ is alkyl of 1 to 6 carbon atoms}, or —CN;

Q represents an aryl group containing from 6 to 15 carbon atoms or an aromatic heterocyclic group containing from 3 to 14 carbon atoms and having at least one O, S, or N in the ring, which aryl or aromatic heterocyclic group can optionally be substituted with up to 3 substituents Y as defined below; and each Y substituent is independently selected form —OH, hydroxymethyl, alkyl containing from 1 to 6 carbon atoms, halo, —N$_2$, alkoxy containing 1 to 6 carbon atoms, —CF$_3$, —CN, cycloalkyl containing 3 to 7 carbon atoms, alkenyloxy containing from 3 to 6 carbon atoms, alkynyloxy containing from 3 to 6 carbon atoms, —S(O)$_p$-R$^4$, {wherein R$^4$ is as defined above and p is an integer of from 0 to 2}, —CO—R$^5$ {wherein R$^5$ represents —OH, —NH$_2$, —NHR$^4$, —N(R$^4$)$_2$ or —OR$^4$ in which R$^4$ is as defined above}, —O—D—COR$^5$, {wherein D represents alkylene having from 1 to 4 carbon atoms and R$^5$ is a defined above}, —NH$_2$, —NHR$^4$, —H(R$^4$)$_2$ {wherein R$^4$ is as defined above} or —NHCOH.

2. A pharmaceutical composition comprising a compound according to claim 1 in combination with a pharmaceutically acceptable carrier.

3. A method of treating an allergic reaction in a mammal comprising administering a compound of formula I as defined in claim 1 in an amount effective to treat an allergic reaction.

4. A method of treating infammation in a mammal comprising administering to said an antiinflammatory effective amount of a compound of formula I as defined in claim 1.

5. A method of treating a peptic ulcer in a mammal comprising administering to said mammal a cytoprotective effective amount of a compound of formula I as defined in claim 1.

6. A method of treating hyperproliferative skin disease in a mammal comprising administering to said mammal and anti-hyperproliferative skin disease effective amount of a compound of formula I as defined in claim 1.

7. A method according to claim 6 wherein the disease is psoriasis, lichenfied eczema or seborrheic dermatitis.

8. A method according to claim 7 wherein the disease is psoriasis.

9. A compound according to claim 1 selected from:

5-phenyl-7,8,9,10-tetrahydro-benzo-naphthyridin-6(5H)-one;

5-(3-chlorophenyl)-7,8,9,10-tetrahydro-benzo-naphthyridin-6(5H)-one; or 1,2-dihydro-2-(hydroxymethyl)-4-phenylcyclobuta(c)-naphthyridin-3(4H)-one.

* * * * *

UNITED STATES PATENT AND TRADEMARK OFFICE
CERTIFICATE OF CORRECTION

PATENT NO. : 4,866,061

DATED : September 12, 1989

INVENTOR(S) : David J. Blythin and Ho-Jane Shue

It is certified that error appears in the above-identified patent and that said Letters Patent is hereby corrected as shown below:

In claim 1, column 24, line 36 "form" should read --from--.

In claim 1, column 24, line 38 "-N$_2$" should read ---NO$_2$--.

In claim 1, column 24, line 49 "H(R$^4$)$_2$" should read -- -N(R$^4$)$_2$--.

In claim 4, column 24, line 58 "infammation" should read --inflammation--.

In claim 7, column 25, line 4 "lichenfied" should read --lichenified--.

In claim 9, column, 26, line 1 "benzo-naphthyridin-" should read -- benzo[c][1,8]-naphthyridin --.

In claim 9, column 26, line 3 "benzo-naph-" should read -- benzo[c][1,8]-naph- --.

In claim 9, column 26, line 5 after "(c)" insert -- [1,8] --.

In claim 4, column 24, line 59 after the word "said" insert -- mammal --.

UNITED STATES PATENT AND TRADEMARK OFFICE
CERTIFICATE OF CORRECTION

PATENT NO. : 4,866,061

DATED : September 12, 1989

INVENTOR(S) : David J. Blythin and Ho-Jane Shue

It is certified that error appears in the above-identified patent and that said Letters Patent is hereby corrected as shown below:

In claim 6, column 24, line 68, delete "and" and insert therefor -- an --.

Signed and Sealed this

Twentieth Day of August, 1991

Attest:

HARRY F. MANBECK, JR.

Attesting Officer

Commissioner of Patents and Trademarks